(12) United States Patent
Soh et al.

(10) Patent No.: US 7,935,856 B2
(45) Date of Patent: May 3, 2011

(54) PREPARATION METHOD OF 1,5-DIMETHYLTETRALIN USING DEALUMINATED ZEOLITE BETA CATALYST

(75) Inventors: Byoung-Whan Soh, Gyeonggi-do (KR); Young-Gyo Choi, Gyeonggi-do (KR)

(73) Assignee: Hyosung Corporation, Seoul (KR)

( * ) Notice: Subject to any disclaimer, the term of this patent is extended or adjusted under 35 U.S.C. 154(b) by 343 days.

(21) Appl. No.: 11/545,866

(22) Filed: Oct. 10, 2006

(65) Prior Publication Data

US 2007/0232842 A1 Oct. 4, 2007

(30) Foreign Application Priority Data

Apr. 4, 2006 (KR) .................... 10-2006-0030397

(51) Int. Cl.
*C07C 2/52* (2006.01)
(52) U.S. Cl. .................. 585/418; 585/407; 585/411
(58) Field of Classification Search .................. 585/410, 585/411, 400
See application file for complete search history.

(56) References Cited

U.S. PATENT DOCUMENTS

| | | | |
|---|---|---|---|
| 4,950,825 A | 8/1990 | Sikkenga et al. | |
| 5,030,781 A | 7/1991 | Sikkenga et al. | |
| 5,034,561 A | 7/1991 | Sikkenga et al. | |
| 5,284,987 A | 2/1994 | Sikkenga et al. | |
| 5,396,008 A * | 3/1995 | Ozawa et al. | 585/411 |
| 5,401,892 A | 3/1995 | Sikkenga et al. | |
| 6,504,069 B1 | 1/2003 | Kyuuko et al. | |
| 2003/0108465 A1 * | 6/2003 | Voss et al. | 423/213.2 |

FOREIGN PATENT DOCUMENTS

| | | |
|---|---|---|
| EP | 0 582 108 B1 | 10/1996 |
| EP | 1 031 550 A1 | 8/2000 |
| JP | 48-96577 | 10/1973 |
| KR | 10-2001-0009664 A | 2/2001 |
| WO | WO 2004058666 A1 * | 7/2004 |

OTHER PUBLICATIONS

Choo, D. et al. "Cycloisomerization of 5-(o-Tolyl)-Pentene over Modified Zeolite BEA", Journal of Catalysis, vol. 207, 2002, pp. 183-193.
Biswas, J. et al. "Recent Process- and Catalyst-Related Developments in Fluid Catalytic Cracking", Applied Catalysis, vol. 63, 1990, pp. 197-258.
Japanese Office Action for corresponding Japanese Patent Application No. 2006-252284, mailed May 24, 2010.

* cited by examiner

*Primary Examiner* — Tam M Nguyen
(74) *Attorney, Agent, or Firm* — Merchant & Gould P.C.

(57) ABSTRACT

The present invention relates to a method for preparing 1,5-dimethyltetralin using a dealuminated zeolite beta catalyst. The preparation method of 1,5-dimethyltetralin according to the present invention has the effects of not only showing high conversion and high selectivity of 1,5-dimethyltetralin but also of suppressing deactivation of a zeolite beta catalyst so as to enhance the catalyst life, by using the dealuminated zeolite beta catalyst.

1 Claim, No Drawings

PREPARATION METHOD OF 1,5-DIMETHYLTETRALIN USING DEALUMINATED ZEOLITE BETA CATALYST

BACKGROUND OF THE INVENTION

1. Field of the Invention

The present invention relates to a method for preparing 1,5-dimethyltetralin using a dealuminated zeolite beta catalyst.

2. Description of the Related Art 1,5-dimethyltetralin (hereinafter referred to as "1,5-DMT") is an intermediate raw material necessary for preparation of polyethylene naphthalate (PEN) and is prepared by the cyclization reaction of 5-ortho-tolylpentene (5-OTP), in particular, 5-(ortho-tolyl)-1-pentene, 5-(ortho-tolyl)-2-pentene or a mixture thereof.

1,5-DMT is subjected to dehydrogenation to form 1,5-dimethylnaphthalene (1,5-DMN) and this 1,5-dimethylnaphthalene is subjected to isomerization to form 2,6-dimethylnaphthalene (2,6-DMN). The isomerization is an equilibrium reaction, which gives 2,6-DMN consisting of an equilibrium composition of 1,6-DMN and 1,5-DMN as isomers thereof, and this 2,6-DMN is then subjected to a purification process using crystallization, as a post-process, to prepare high purity 2,6-DMN. The above 2,6-DMN is subjected to oxidation and hydrogenation to prepare 2,6-naphthalenedicarboxylic acid (2,6-NDA) serving as a raw material for polyethylene naphthalate.

A general method for preparing 2,6-naphthalenedicarboxylic acid (2,6-NDA) from the above-mentioned 5-ortho-tolylpentene (5-OTP) is represented by the following reaction scheme 1:

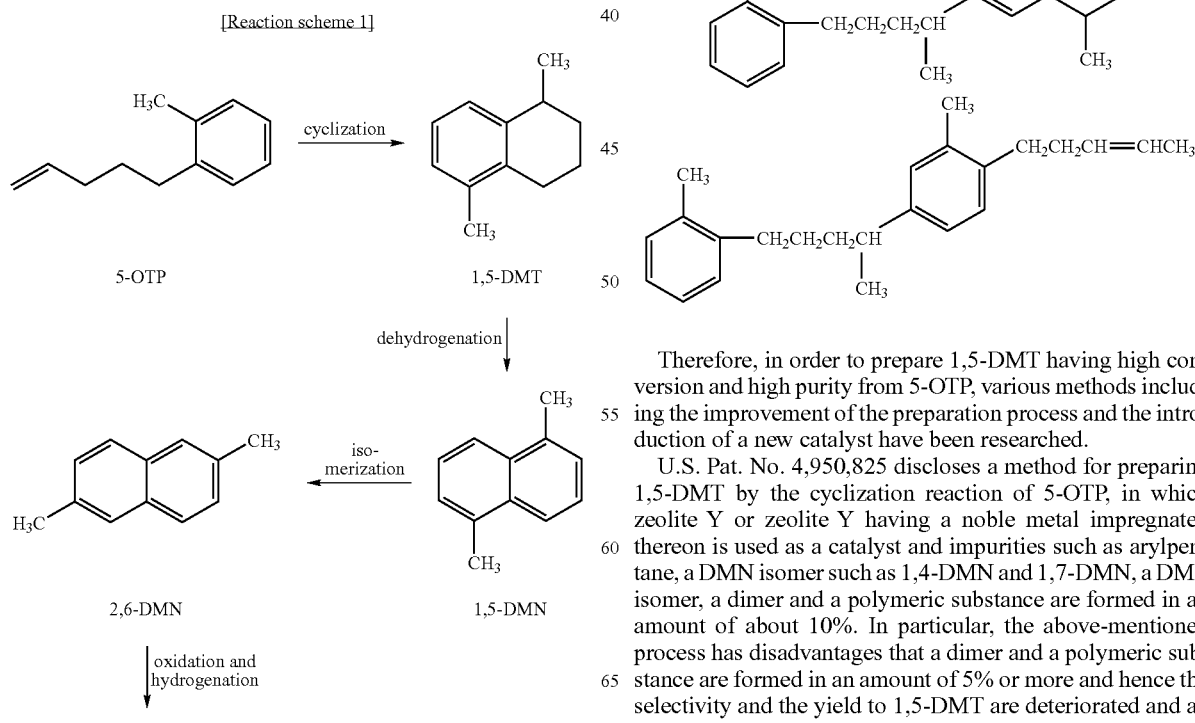

Polyethylene naphthalate (PEN) can be used in the applications of a large capacity magnetic tape capable of recording for a long time, a heat resistant capacitor, a tire cord and a container for drinks because it is excellent in thermal, mechanical, chemical and electrical properties, as well as in physical properties such as water resistance and air permeation resistance, as compared with polyethylene terephthalate (PET) which is currently widely used as a general purpose resin, and thus the demands of the polyethylene naphthalate tend to gradually increase.

Therefore, many researches on the preparation of 1,5-DMT, which is an intermediate raw material of polyethylene naphthalate, have been conducted. However, the related art regarding the preparation of 1,5-DMT from 5-OTP has disadvantages that a large amount of impurities are formed and hence an additional process for separating the impurities is required. Examples of the impurities formed in this case include a dimethylnaphthalene (DMN) isomer, a dimethyltetralin (DMT) isomer, a dimer and a polymeric substance. The term "dimer" as used herein refers to a substance having a molecular weight of 320 includes a dimer of reactants or reaction products. Examples of the dimer include a dimer of 5-OTP and 1,5-DMT and a dimer of two molecules of 5-OTP.

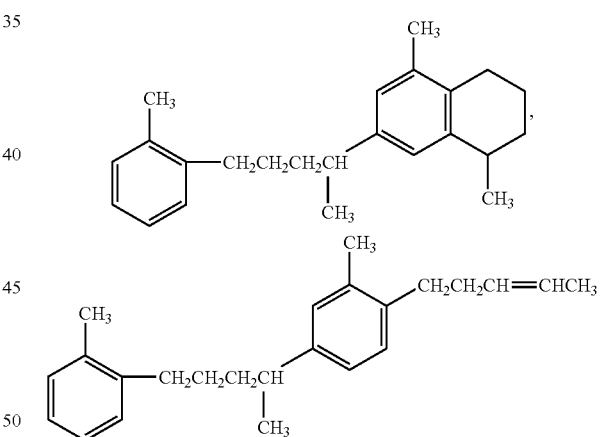

Therefore, in order to prepare 1,5-DMT having high conversion and high purity from 5-OTP, various methods including the improvement of the preparation process and the introduction of a new catalyst have been researched.

U.S. Pat. No. 4,950,825 discloses a method for preparing 1,5-DMT by the cyclization reaction of 5-OTP, in which zeolite Y or zeolite Y having a noble metal impregnated thereon is used as a catalyst and impurities such as arylpentane, a DMN isomer such as 1,4-DMN and 1,7-DMN, a DMT isomer, a dimer and a polymeric substance are formed in an amount of about 10%. In particular, the above-mentioned process has disadvantages that a dimer and a polymeric substance are formed in an amount of 5% or more and hence the selectivity and the yield to 1,5-DMT are deteriorated and an additional separation process is required.

Further, U.S. Pat. No. 5,034,561 discloses a method for preparing 1,5-DMT by the cyclization reaction of 5-OTP, in which an ultrastable, Y-type zeolite (hereinafter referred to as a "USY") catalyst is used as a catalyst and it further comprises a process that a distillation column is provided at the rear end of the reactor for the purpose of separating 1,5-DMT, and thus 1,5-DMT having an improved purity is obtained. U.S. Pat. Nos. 5,030,781 and 5,401,892 also disclose that the USY catalyst was used as a catalyst. Furthermore, U.S. Pat. No. 5,284,987 discloses that a zeolite catalyst such as mordenite, zeolite X, zeolite Y and ZSM-5 was used as the cyclization catalyst of 5-OTP. U.S. Pat. No. 6,504,069 B1 and European Patent No. 1 031 550 A1 disclose a method for preparing 1,5-DMT by introducing various new catalysts including a catalyst prepared by impregnating a carrier such as zeolite, silica-alumina, silica-zirconia and silica-titania with sulfuric acid or phosphoric acid, in order to attempt an improvement on the reactivity. However, these patents have disadvantages that the formation of impurities such as a DMT isomer, a DMN isomer and a polymeric substance were not decreased and the yield of 1,5-DMT was largely lowered when the reaction temperature was decreased so as to inhibit the formation of the impurities. Further, the impurities formed lead to a decrease in the catalyst selectivity and have significant adverse effects such as deterioration in catalyst activity and a decrease in catalyst life.

Korean Patent No. 10-0303246 discloses a method for selectively preparing 1,5-DMT by the cyclization reaction of 5-ortho-tolylpentene using a zeolite beta catalyst. However, this process exhibits a high conversion and a high selectivity to 1,5-DMT at the initial reaction, but has a problem that the catalyst life becomes reduced due to the significant deactivation of the catalyst and a problem that it is difficult to industrially apply this process with the use of the zeolite beta catalyst in the form of powders.

In general, it is known that the deterioration in catalyst activity and the decrease in catalyst life are caused by poisoning from a product and impurities in the reaction of a hydrocarbon compound [Appl. Catal. 63, 197 (1990)].

U.S. Pat. No. 5,396,008 and European Patent No. 0 582 108 B1 disclose a method for preparing 1,5-DMT by the cyclization reaction of 5-OTP with a high conversion and a high selectivity, and an improved catalyst life, in which the cyclization reaction of 5-OTP is carried out in gaseous state in the presence of a diluent by the use of a catalyst comprising a weakly acidic carrier such as activated carbon, silica, titania and zirconia and aluminosilicate impregnated thereon, in order to prevent the deactivation of the catalyst and the decrease in catalyst life. However, the method has disadvantages that it further comprises a process of mixing and extruding the carrier and the catalyst substance for industrially applicability and also has problems that process deviation conditions may occur caused by the diluent and it requires a high cost because the reaction is carried out at high temperatures so as to maintain the reaction system in a gaseous state.

On the other hand, according to the related art, it is known that the cyclization reaction of 5-OTP to 1,5-DMT using a zeolite beta catalyst takes place at two active sites. It is reported that an isomerization reaction and a polymer reaction take place at the acid site existing on the external surface of the catalyst to form DMTs other than 1,5-DMT and the cyclization reaction to 1,5-DMT takes place at the acid site existing on the internal surface of the catalyst [J. Catal., 207, 183 (2002)].

Therefore, it is expected that the removal of active sites existing on the external surface of the zeolite beta catalyst will have considerable influence on the improvement on catalyst life.

In this regard, the present inventors have studied on a method for preparing 1,5-dimethyltetralin which has a high conversion and a high selectivity, and allows suppression of catalyst deactivation and improvement on catalyst life, and have found that the cyclization reaction of 5-OTP is carried out using a zeolite beta catalyst in which the active sites existing on the external surface thereof are selectively removed by dealumination, to obtain a high conversion and a high selectivity of 1,5-dimethyltetralin and to suppress deactivation of the zeolite beta catalyst, thereby improving catalyst life. Thus, they have completed the present invention.

SUMMARY OF THE INVENTION

Accordingly, an object of the present invention is to provide a method for preparing 1,5-dimethyltetralin using a dealuminated zeolite beta catalyst.

DESCRIPTION OF THE PREFERRED EMBODIMENTS

The present invention provides a method for preparing 1,5-dimethyltetralin by the cyclization reaction of 5-ortho-tolylpentene using a dealuminated zeolite beta.

The above and other features and advantages of the present invention will become more apparent by describing in detail preferred embodiments thereof.

The zeolite beta catalyst used in the preparation method of 1,5-dimethyltetralin according to the present invention is characterized in that the sodium ion form of the zeolite beta catalyst is replaced by an ammonium ion form thereof and then calcined to convert the ammonium ion form into a hydrogen ion form thereof, and the resultant catalyst is dealuminated by treating with acids.

The term "dealumination" refers to the partial removal of aluminum atoms from silicon and aluminum atoms as main zeolite crystal-forming elements in the crystal lattice without significantly impacting the crystal structure. The strength and amount of acid sites vary depending on the extent of the dealumination.

A method for preparing the dealuminated zeolite beta catalyst is described in detail below.

The sodium ion form of the zeolite beta catalyst is dipped into 10 to 50 wt % of 1 N ammonium nitrate ($NH_4NO_3$) and is stirred at 70 to 95° C. for 10 to 40 hours at a stirring rate of 100 to 500 rpm. The ammonium ion-exchanged form of the zeolite beta catalyst is sufficiently washed with distilled water until pH 6.0 to 7.0 is reached and then dried in a dryer at a temperature of 100 to 150° C. for 10 to 30 hours to prepare an ammonium form of the zeolite beta catalyst.

Thus prepared ammonium form of the zeolite beta catalyst is heated from room temperature to 500° C. at a heating rate of 10° C./min and maintained at 500° C. for 2 to 10 hours, followed by naturally cooling to room temperature to prepare a hydrogen ion form of the zeolite beta catalyst.

The hydrogen ion form of the zeolite beta catalyst produced is dealuminated by treating with acids. Examples of the acid usable in this case include nitric acid, hydrochloric acid, sulfuric acid and phosphoric acid and of these, nitric acid is most preferred. For example, the hydrogen ion form of the zeolite beta catalyst is dipped into 10 to 50 wt % of a 0.5 to 2 N aqueous nitric acid ($HNO_3$, 60%) solution and is stirred at 70 to 95° C. for 5 to 20 hours, and preferably 8 to 12 hours at a stirring rate of 100 to 500 rpm to remove aluminum. A dealuminated zeolite beta catalyst is sufficiently washed with distilled water until pH 6.0 to 7.0 is reached and aluminum eluted from the remaining nitric acid solution and the crystal lattice is removed. Thereafter, the catalyst is dried in a dryer at a temperature of 100 to 150° C. for 10 to 30 hours. Then, the catalyst is heated from room temperature to 550° C., preferably from room temperature to 500° C. at a rate of 10° C./min and maintained at 500° C. for 2 to 10 hours, preferably 4 to 8 hours, followed by naturally cooling to room temperature to produce the dealuminated zeolite beta catalyst. In this case, when the concentration of nitric acid is less than 0.5 N, dealumination is not properly conducted. When the concentration of nitric acid is more than 2 N, excessive dealumination can result in the destruction of the beta structure. Further, when the temperature of the aqueous solution during dealumination is less than 70° C., dealumination is not sufficiently conducted within 8 to 12 hours, whereas when it exceeds 95° C., it is not suitable for dealumination because water in the aqueous solution phase is rapidly evaporated.

The dealuminated zeolite beta catalyst preferably has a $SiO_2/Al_2O_3$ molar ratio of 10 to 150 and specific surface area of 400 to 600 m$^2$/gr. When the zeolite beta catalyst having a $SiO_2/Al_2O_3$ molar ratio of about 5 before dealumination is subjected to dealumination so as to have a $SiO_2/Al_2O_3$ molar ratio of 10 or less, the deactivation of the catalyst is not prevented. When the $SiO_2/Al_2O_3$ molar ratio is more than 150, the zeolite beta structure in the dealuminated catalyst is destroyed.

In general, it is not easy to obtain accurate experimental results since the cyclization reaction of 5-OTP is a severe exothermic reaction (reaction enthalpy≈22 kcal/mol) to cause a problem for temperature control during the reaction.

Accordingly, in the present invention, variation between initial activities of the catalysts and activities after the deactivation thereof is determined while maintaining a constant temperature during the reaction by using o-xylene as a diluent. Further, in order to compare actual activities of the catalysts, the reaction experiment is performed by using only 5-OTP as a reactant without o-xylene.

Specifically, 5-OTP mixed with 0.1 to 90 wt % of o-xylene is put in a liquid-phase batch reactor and the reaction conditions are 80 to 250° C. at normal pressure. The dealuminated zeolite catalyst is introduced into the reactants in an amount of about 10 to 60 wt % relative to 5-OTP to react with stirring at 100 to 500 rpm. In this case, when the amount of the catalyst exceeds 60 wt %, variation in the deactivation of the catalyst is not easy to observe since the cyclization reaction of 5-OTP is mostly conducted in the initial reaction stage, and when the amount of the catalyst is less than 10 wt %, the conversion of total 5-OTP as reactants requires much time and side-reaction products may be further generated as the residence time of the product in the reactor increases. The initial reactants are introduced to observe variation in the activities of the catalyst for 28 hours. Thereafter, the catalyst remains in the liquid-phase batch reactor and only the product is removed therefrom. Then, fresh reactants are added to the reactor in the same proportions as those of the initial reactants to carry out an experiment under the same reaction conditions as those in the reaction experiment of the initial reactants, such as a temperature, a pressure and a stirring rate. With regard to each catalyst, experiments are repeated four times under the same reaction conditions to observe variation in the activities of the catalysts.

Further, one experiment is carried out using only 5-OTP without a diluent, as the reactants, under the same reaction conditions as those described above, such as a temperature, a pressure, or the like to compare the activities of the catalysts. In this case, when the reaction temperature is lower than 80° C., a decrease in the reaction rate results in a decrease in reaction activities, whereas when it is higher than 250° C., the side reaction results in a rapid decrease of the selectivity.

The o-xylene serving as a diluent does not affect the cyclization reaction of 5-OTP. A large amount of the diluent makes it more favorable in controlling of the reactor temperature, but it is not preferred in that when the diluent is present in an amount of 90 wt % or more, it affects the reaction yield.

Examples of 5-ortho-tolylpentene used in the present invention include 5-(ortho-tolyl)-1-pentene, 5-(ortho-tolyl)-2-pentene, 5-(ortho-tolyl)-3-pentene, 5-(ortho-tolyl)-4-pentene, or a mixture thereof.

In the preparation method of 1,5-dimethyltetralin according to the present invention, the reactants is used in a gaseous or liquid state. The reaction can be carried out in various modes such as a continuous stirred tank reaction (CSTR) mode, and a plug flow reaction (tubular reaction; PFR) mode, in addition to a batch mode. If the reaction is carried out in the tubular reaction (PFR) mode, the nitrogen gases first pass through the reactor to remove air in the reactor and then the cyclization reaction is conducted at the reaction temperature of 70 to 450° C., preferably 70 to 220° C. and the reaction pressure of 0.04 to 30 atms, preferably 0.1 to 2 atms, and a weight hour space velocity (WHSV), i.e., (5-OTP [g]/catalyst [g]×time [hr]) of 0.01 to 200/hr, preferably 0.1 to 10/hr.

In the present invention, the reactants and product were collected and analyzed over the reaction time by gas chromatography (Model No.: 6890N, manufactured by Agilent Technologies). The conversion of 5-OTP, the selectivity of 1,5-DMT and yield are represented by the following formulas:

$$\text{Conversion (\%)} = \frac{A-B}{A} \times 100$$

$$\text{Selectivity (\%)} = \frac{C}{A-B} \times 100$$

$$\text{Yield (\%)} = \frac{\text{conversion ratio (\%)}}{100} \times \frac{\text{selectivity (\%)}}{100} \times 100$$

wherein A represents the concentration of 5-OTP before reaction; B represents the concentration of 5-OTP after reaction; and C represents the concentration of 1,5-DMT formed.

In the preparation method of 1,5-dimethyltetralin according to the present invention, deactivation of the catalyst is suppressed and thus catalyst life is improved, and a high conversion and high selectivity of 1,5-dimethyltetralin are exhibited even after a lapse of time by the use of the dealuminated zeolite beta catalyst, as compare with the use of an ultrastable, Y-type zeolite (USY) catalyst, a zeolite beta catalyst having undergone no dealumination treatment, or a zeolite beta catalyst having platinum and copper supported thereon, which have been used in the related art.

Hereinafter, preferred Examples are presented in order to facilitate understanding of the present invention. However, the following Examples are provided only for the purpose of allowing easier understanding of the present invention, and are not intended to limit the present invention in any way.

The zeolite beta catalyst used in the following Example was HSZ-930H (manufactured by Tosoh Corporation, Japan) having a $SiO_2/Al_2O_3$ molar ratio of 5 to 10, an average particle size of 1.5 mm, a specific surface area of 400 to 500 m$^2$/gr. The 5-OTP used was a product (trade name: CAS No. 6047-69-4, manufactured by Aldrich) having a purity of 98%.

Examples 1 to 4

Preparation of 1,5-dimethyltetralin (1,5-DMT) Using Dealuminated Zeolite Beta Catalyst According to the Present Invention

Example 1

1. Preparation of Dealuminated Zeolite Beta Catalyst

Thirty-two grams of the hydrogen ion form of the zeolite beta catalyst ($SiO_2/Al_2O_3=5$) dried at 120° C. 12 hours was dipped into 300 ml of a 0.8 N aqueous nitric acid ($HNO_3$, 60%) solution at 90° C. and stirred for 8 hours at a stirring rate of 200 rpm. The supernatant was removed, and a dealuminated zeolite beta catalyst was sufficiently washed with distilled water until pH 6.5 was reached and aluminum eluted from the remaining nitric acid solution and the crystal lattice was removed. Thereafter, the catalyst was dried in a dryer at 120° C. for 13 hours. Then, the catalyst is heated from room temperature to 500° C. at a rate of 10° C./min and maintained at 500° C. for 6 hours, followed by naturally cooling to room temperature to produce the dealuminated zeolite beta catalyst.

By the above-mentioned process, a dealuminated zeolite beta catalyst having a $SiO_2/Al_2O_3$ molar ratio of 14 was prepared from the hydrogen ion form of the zeolite beta catalyst having a $SiO_2/Al_2O_3$ molar ratio of 5.

2. Preparation of 1,5-dimethyltetralin

Three hundred milliliters of a solution obtained by mixing o-xylene as a diluent and 5-OTP as a reactant in a weight ratio of 9:1 was introduced into a liquid-phase batch reactor. Then, the mixture was heated to 120° C. at normal pressure by using a mantle. Thereafter, 9 g of the dealuminated zeolite beta catalyst prepared in the above 1 was added to the reaction solution and the resulting mixture was allowed to react under stirring at 200 rpm for 28 hours while maintaining the reaction temperature at 120° C.±1° C. The concentration of the product over the reaction time was analyzed by gas chromatography (Model No.: 6890N, manufactured by Agilent Technologies). The analyzed results for the product were shown in Table 1.

As shown in Table 1, the conversion and the selectivity were 94.0% and 88.8% at 30 minutes and 100% and 86.0% at 1 hour after initiation of the reaction, respectively, and the selectivity was 84.4% at 28 hours after initiation of the reaction.

Example 2

1,5-DMT was prepared by the cyclization reaction under the same reaction conditions as in Example 1-2, except that the catalyst remained after completion of the reaction of Example 1 was left in a liquid-phase batch reactor and only the product was removed, and then fresh reactants were introduced into the reactor for reaction. The product was analyzed by gas chromatography and the results thereof were shown in Table 1.

As shown in Table 1, the conversion and the selectivity were 93.4% and 91.4% at 30 minutes and 100% and 90.4% at 1 hour after initiation of the reaction, respectively, and the selectivity was 87.1% at 28 hours after initiation of the reaction.

Example 3

1,5-DMT was prepared by the cyclization reaction under the same reaction conditions as in Example 1-2, except that the catalyst remained after completion of the reaction of Example 2 was left in a liquid-phase batch reactor and only the product was removed, and then fresh reactants were introduced into the reactor for reaction. The product was analyzed by gas chromatography and the results thereof were shown in Table 1.

As shown in Table 1, the conversion and the selectivity were 69.7% and 95.5% at 30 minutes, 93.3% and 91.5% at 1 hour, and 100% and 88.6% at 2 hours after initiation of the reaction, respectively, and the selectivity was 87.1% at 28 hours after initiation of the reaction.

Example 4

1,5-DMT was prepared by the cyclization reaction under the same reaction conditions as in Example 1-2, except that the catalyst remained after completion of the reaction of Example 3 was left in a liquid-phase batch reactor and only the product was removed, and then fresh reactants were introduced into the reactor for reaction. The product was analyzed by gas chromatography and the results thereof were shown in Table 1.

As shown in Table 1, the conversion and the selectivity were 54.9% and 100% at 30 minutes, 86.4% and 96.0% at 1 hour, and 97.3% and 92.5% at 2 hours after initiation of the reaction, respectively, and the selectivity was 87.9% at 28 hours after initiation of the reaction.

TABLE 1

|  | Reaction time (hrs) | Example 1 | Example 2 | Example 3 | Example 4 |
|---|---|---|---|---|---|
| Conversion (%) | 0.5 | 94.0 | 93.4 | 69.7 | 54.9 |
|  | 1 | 100 | 100 | 93.3 | 86.4 |
|  | 2 | 100 | 100 | 100 | 97.3 |
|  | 28 | 100 | 100 | 100 | 100 |
| Selectivity (%) | 0.5 | 88.8 | 91.4 | 95.5 | 100 |
|  | 1 | 86.0 | 90.4 | 91.5 | 96.0 |
|  | 2 | 86.5 | 89.2 | 88.6 | 92.5 |
|  | 28 | 84.4 | 88.7 | 87.1 | 87.9 |
| Yield (%) | 0.5 | 83.5 | 85.4 | 66.6 | 54.9 |
|  | 1 | 86.0 | 90.4 | 85.4 | 82.9 |
|  | 2 | 86.5 | 89.2 | 88.6 | 90.0 |
|  | 28 | 84.4 | 88.7 | 87.1 | 87.9 |
| Reaction temperature (° C.) |  | 120 | 120 | 120 | 120 |
| Cumulative reaction time (hrs) |  | 28 | 56 | 84 | 112 |

Comparative Examples 1 to 4

Preparation of 1,5-dimethyltetralin (1,5-DMT) Using Zeolite Beta Catalyst Having Undergone no Dealumination Treatment

Comparative Example 1

1,5-DMT was prepared by the cyclization reaction under the same reaction conditions as in Example 1-2, except that the hydrogen ion form of the zeolite beta catalyst ($SiO_2/Al_2O_3=7$) calcined at 500° C. for 4 hours and dried at 120° C. for 12 hours was used.

The concentration of the product over the reaction time was analyzed by gas chromatography and the results thereof were shown in Table 2.

As shown in Table 2, the conversion and the selectivity were 50.6% and 93.3% at 30 minutes, 72.4% and 89.7% at 1 hour, and 100% and 86.1% at 4 hours after initiation of the reaction, respectively, and the selectivity was 81.4% at 28 hours after initiation of the reaction.

Comparative Example 2

1,5-DMT was prepared by the cyclization reaction under the same reaction conditions as in Example 1-2, except that the catalyst remained after completion of the reaction of Comparative Example 1 was left in a liquid-phase batch reactor and only the product was removed, and then fresh reactants were introduced into the reactor for reaction.

The concentration of the product over the reaction time was analyzed by gas chromatography and the results thereof were shown in Table 2.

As shown in Table 2, the conversion and the selectivity were 32.1% and 100% at 30 minutes and 43.2% and 93.5% at 1 hour after initiation of the reaction. Only at 10 hours after initiation of the reaction, the conversion was 100% and the selectivity was 89.2%. The selectivity was 82.5% at 28 hours after initiation of the reaction.

Comparative Example 3

1,5-DMT was prepared by the cyclization reaction under the same reaction conditions as in Example 1-2, except that the catalyst remained after completion of the reaction of Comparative Example 2 was left in a liquid-phase batch reactor and only the product was removed, and then fresh reactants were introduced into the reactor for reaction.

The concentration of the product over the reaction time was analyzed by gas chromatography and the results thereof were shown in Table 2.

As shown in Table 2, the conversion and the selectivity were 20.8% and 100% at 30 minutes, and 31.4% and 100% at 1 hour after initiation of the reaction. Only at 18 hours after initiation of the reaction, the conversion was 100% and the selectivity was 90.7%. The selectivity was 89.1% at 28 hours after initiation of the reaction.

Comparative Example 4

1,5-DMT was prepared by the cyclization reaction under the same reaction conditions as in Example 1-2, except that the catalyst remained after completion of the reaction of Comparative Example 3 was left in a liquid-phase batch reactor and only the product was removed, and then fresh reactants were introduced into the reactor for reaction.

The concentration of the product over the reaction time was analyzed by gas chromatography and the results thereof were shown in Table 2.

As shown in Table 2, the conversion and the selectivity were 13.2% and 100% at 30 minutes and 18.4% and 100% at 1 hour after initiation of the reaction, respectively. Even at 28 hours after initiation of the reaction, the conversion of 100% was not obtained, and the conversion and the selectivity were 96.5% and 93.5%, respectively.

TABLE 2

|  | Reaction time (hrs) | Comp. Ex. 1 | Comp. Ex. 2 | Comp. Ex. 3 | Comp. Ex. 4 |
|---|---|---|---|---|---|
| Conversion (%) | 0.5 | 50.6 | 32.1 | 20.8 | 13.2 |
|  | 1 | 72.4 | 43.2 | 31.4 | 18.4 |
|  | 4 | 100 | 100* | 100** | 40.8 |
|  | 28 | 100 | 100 | 100 | 96.5 |
| Selectivity (%) | 0.5 | 93.3 | 100 | 100 | 100 |
|  | 1 | 89.7 | 93.5 | 100 | 100 |
|  | 4 | 86.1 | 89.2* | 90.7** | 100 |
|  | 28 | 81.4 | 82.5 | 89.1 | 93.5 |
| Yield (%) | 0.5 | 47.2 | 32.1 | 20.8 | 13.2 |
|  | 1 | 64.9 | 40.4 | 31.4 | 48.4 |
|  | 4 | 86.1 | 89.2 | 90.7 | 40.8 |
|  | 28 | 81.4 | 82.5 | 89.1 | 90.2 |
| Reaction temperature (° C.) |  | 120 | 120 | 120 | 120 |
| Cumulative reaction time (hrs) |  | 28 | 56 | 84 | 112 |

(Note)
*Results of analysis at 10 hours after initiation of the reaction,
**Results of analysis at 18 hours after initiation of the reaction

Comparative Examples 5 to 8

Preparation of 1,5-dimethyltetralin (1,5-DMT) Using Platinum and Copper Ion-Exchanged Zeolite Beta Catalyst

Comparative Example 5

1. Preparation of Platinum and Copper Ion-Exchanged Zeolite Beta Catalyst

Sixteen grams of the hydrogen ion form of the zeolite beta catalyst dried at 120° C. for 12 hours were dipped into 300 ml of an aqueous solution at 90° C. where 0.65 g of chloroplatinic acid ($H_2PtCl_6 6H_2O$) and 1.3 g of $Cu(NO_3)_2 3H_2O$ are dissolved in water and stirred for 4 hours at a stirring rate of 300 rpm. The supernatant was removed, and a platinum and copper ion-exchanged zeolite beta catalyst was sufficiently washed with distilled water until pH 6.5 was reached. Thereafter, the catalyst was dried in a dryer at 120° C. for 13 hours. Then, the catalyst is heated from room temperature to 500° C. at a rate of 10° C./min and maintained at 500° C. for 6 hours, followed by naturally cooling to room temperature to produce the platinum and copper ion-exchanged zeolite beta catalyst.

2. Preparation of 1,5-dimethyltetralin

The cyclization reaction of 5-OTP was carried out under the same reaction conditions as in Example 1-2, using the platinum and copper ion-exchanged zeolite beta catalyst prepared in the above 1.

The concentration of the product over the reaction time was analyzed by gas chromatography and the results thereof were shown in Table 3.

As shown in Table 3, the conversion and the selectivity were 40.1% and 100% at 30 minutes and 56.4% and 84.3% at 1 hour after initiation of the reaction, respectively. Only after 8 hours since initiation of the reaction, the conversion was 100% and the selectivity was 81.8%. The selectivity was 81.3% at 28 hours after initiation of the reaction.

Comparative Example 6

1,5-DMT was prepared by the cyclization reaction under the same reaction conditions as in Example 1-2, except that the catalyst remained after completion of the reaction of Comparative Example 5 was left in a liquid-phase batch reactor and only the product was removed, and then fresh reactants were introduced into the reactor for reaction.

The concentration of the product over the reaction time was analyzed by gas chromatography and the results thereof were shown in Table 3.

As shown in Table 3, the conversion and the selectivity were 11.0% and 100% at 30 minutes and 22.3% and 100% at 1 hour after initiation of the reaction, respectively. Even at 28 hours after initiation of the reaction, the conversion of 100% was not obtained, and the conversion and the selectivity were 96.9% and 93.6%, respectively.

Comparative Example 7

1,5-DMT was prepared by the cyclization reaction under the same reaction conditions as in Example 1-2, except that the catalyst remained after completion of the reaction of Comparative Example 6 was left in a liquid-phase batch reactor and only the product was removed, and then fresh reactants were introduced into the reactor for reaction.

The concentration of the product over the reaction time was analyzed by gas chromatography and the results thereof were shown in Table 3.

As shown in Table 3, the conversion and the selectivity were 4.7% and 100% at 30 minutes and 9.1% and 100% at 1 hour after initiation of the reaction, respectively. Even at 28 hours after initiation of the reaction, the conversion of 100% was not obtained, and the conversion and the selectivity were 76.8% and 100%, respectively.

Comparative Example 8

1,5-DMT was prepared by the cyclization reaction under the same reaction conditions as in Example 1-2, except that the catalyst remained after completion of the reaction of Comparative Example 7 was left in a liquid-phase batch reactor and only the product was removed, and then fresh reactants were introduced into the reactor for reaction.

The concentration of the product over the reaction time was analyzed by gas chromatography and the results thereof were shown in Table 3.

As shown in Table 3, the conversion and the selectivity were 1.9% and 100% at 30 minutes and 7.0% and 100% at 1 hour after initiation of the reaction, respectively. Even at 28 hours after initiation of the reaction, the conversion of 100% was not obtained, and the conversion and the selectivity were 59.0% and 100%, respectively.

TABLE 3

|  | Reaction time (hrs) | Comp. Ex. 5 | Comp. Ex. 6 | Comp. Ex. 7 | Comp. Ex. 8 |
|---|---|---|---|---|---|
| Conversion (%) | 0.5 | 40.1 | 11.0 | 4.7 | 1.9 |
|  | 1 | 56.4 | 22.3 | 9.1 | 7.0 |
|  | 8 | 100 | 70.8 | 33.3 | 20.7 |
|  | 28 | 100 | 96.9 | 76.8 | 59.0 |
| Selectivity (%) | 0.5 | 100 | 100 | 100 | 100 |
|  | 1 | 84.3 | 100 | 100 | 100 |
|  | 8 | 81.8 | 100 | 100 | 100 |
|  | 28 | 81.3 | 93.6 | 100 | 100 |
| Yield (%) | 0.5 | 40.1 | 11.0 | 4.7 | 1.9 |
|  | 1 | 47.5 | 22.3 | 9.1 | 7.0 |
|  | 8 | 81.8 | 70.8 | 33.3 | 20.7 |
|  | 28 | 81.3 | 90.7 | 76.8 | 59.0 |

TABLE 3-continued

| Reaction time (hrs) | Comp. Ex. 5 | Comp. Ex. 6 | Comp. Ex. 7 | Comp. Ex. 8 |
|---|---|---|---|---|
| Reaction temperature (° C.) | 120 | 120 | 120 | 120 |
| Cumulative reaction time (hrs) | 28 | 56 | 84 | 112 |

Examples 5 to 8

Preparation of 1,5-dimethyltetralin (1,5-DMT) Using Dealuminated Zeolite Beta Catalyst According to the Present Invention Example 5

1. Preparation of Dealuminated Zeolite Beta Catalyst

A dealuminated zeolite beta catalyst having a $SiO_2/Al_2O_3$ molar ratio of 10 was prepared from the hydrogen ion form of the zeolite beta catalyst having a $SiO_2/Al_2O_3$ molar ratio of 5, in the same manner as in Example 1-1 except that in Example 1-1, 30 g of the hydrogen ion form of the zeolite beta catalyst ($SiO_2/Al_2O_3$=5) dried at 120° C. 12 hours was dipped into 300 ml of a 0.5 N aqueous nitric acid ($HNO_3$, 60%) solution at 90° C.

2. Preparation of 1,5-dimethyltetralin 1,5-DMT was prepared by the cyclization reaction of 5-OTP under the same reaction conditions as in Example 1-2 using the dealuminated zeolite beta catalyst prepared in the above 1.

The concentration of the product over the reaction time was analyzed by gas chromatography and the results thereof were shown in Table 4.

As shown in Table 4, the conversion and the selectivity were 75.7% and 90.2% at 30 minutes, 89.8% and 88.1% at 1 hour, and 100% and 86.4% at 3 hours after initiation of the reaction, respectively, and the selectivity was 82.3% at 28 hours after initiation of the reaction.

Example 6

1,5-DMT was prepared by the cyclization reaction under the same reaction conditions as in Example 1-2, except that the catalyst remained after completion of the reaction of Example 5 was left in a liquid-phase batch reactor and only the product was removed, and then fresh reactants were introduced into the reactor for reaction.

The concentration of the product over the reaction time was analyzed by gas chromatography and the results thereof were shown in Table 4.

As shown in Table 4, the conversion and the selectivity were 33.0% and 100% at 30 minutes, 70.0% and 91.3% at 1 hour, and 100% and 88.2% at 4 hours after initiation of the reaction, respectively, and the selectivity was 86.3% at 28 hours after initiation of the reaction.

Example 7

1,5-DMT was prepared by the cyclization reaction under the same reaction conditions as in Example 1-2, except that the catalyst remained after completion of the reaction of Example 6 was left in a liquid-phase batch reactor and only the product was removed, and then fresh reactants were introduced into the reactor for reaction.

The concentration of the product over the reaction time was analyzed by gas chromatography and the results thereof were shown in Table 4.

As shown in Table 4, the conversion and the selectivity were 21.1% and 100% at 30 minutes, 51.6% and 100% at 1 hour, and 100% and 90.8% at 9 hours after initiation of the reaction, respectively, and the selectivity was 89.1% at 28 hours after initiation of the reaction.

Example 8

1,5-DMT was prepared by the cyclization reaction under the same reaction conditions as in Example 1-2, except that the catalyst remained after completion of the reaction of Example 7 was left in a liquid-phase batch reactor and only the product was removed, and then fresh reactants were introduced into the reactor for reaction.

The concentration of the product over the reaction time was analyzed by gas chromatography and the results thereof were shown in Table 4.

As shown in Table 4, the conversion and the selectivity were 15.5% and 100% at 30 minutes, 28.9% and 100% at 1 hour, and 100% and 93.1% at 23 hours after initiation of the reaction, respectively, and the selectivity was 92.5% at 28 hours after initiation of the reaction.

TABLE 4

|  | Reaction time (hrs) | Example 5 | Example 6 | Example 7 | Example 8 |
|---|---|---|---|---|---|
| Conversion (%) | 0.5 | 75.7 | 33.0 | 21.1 | 15.5 |
|  | 1 | 89.8 | 70.0 | 51.6 | 28.9 |
|  | 3 | 100 | 100* | 100** | 100*** |
|  | 28 | 100 | 100 | 100 | 100 |
| Selectivity (%) | 0.5 | 90.2 | 100 | 100 | 100 |
|  | 1 | 88.1 | 91.3 | 100 | 100 |
|  | 3 | 86.4 | 88.2* | 90.8** | 93.1*** |
|  | 28 | 82.3 | 86.3 | 89.1 | 92.5 |
| Yield (%) | 0.5 | 68.3 | 33.0 | 21.1 | 15.5 |
|  | 1 | 79.1 | 63.9 | 51.6 | 28.9 |
|  | 3 | 86.4 | 88.2 | 90.8 | 93.1 |
|  | 28 | 82.3 | 86.3 | 89.1 | 92.5 |
| Reaction temperature (° C.) |  | 120 | 120 | 120 | 120 |
| Cumulative reaction time (hrs) |  | 28 | 56 | 84 | 112 |

(Note)
*Results of analysis at 4 hours after initiation of the reaction,
**Results of analysis at 9 hours after initiation of the reaction,
***Results of analysis at 23 hours after initiation of the reaction Example 9

1,5-DMT was prepared by the cyclization reaction of 5-OTP under the same reaction conditions as in Example 1-2, except that in Example 1, the diluent was not used, 100 ml of 5-OTP as a reactant was used and 30 g of the dealuminated zeolite beta catalyst was used.

The concentration of the product over the reaction time was analyzed by gas chromatography and the results thereof were shown in Table 5.

As shown in Table 5, the conversion and the selectivity were 92.2% and 91.6% at 30 minutes and 100% and 90.8% at 1 hour after initiation of the reaction, respectively, and the selectivity was 85.1% at 28 hours after initiation of the reaction.

Example 10

1. Preparation of Dealuminated Zeolite Beta Catalyst

A dealuminated zeolite beta catalyst was prepared in the same manner as in Example 1-1, except that in Example 1-1, 32 g of the hydrogen ion form of the zeolite beta catalyst ($SiO_2/Al_2O_3=5$) was replaced by 12 g of the hydrogen ion form of the zeolite beta catalyst ($SiO_2/Al_2O_3=5$), the 0.8 N aqueous nitric acid ($HNO_3$, 60%) solution was replaced by 1 N aqueous nitric acid ($HNO_3$, 60%) solution and pH 6.5 was replaced by pH 7.0.

By the above-mentioned process, a dealuminated zeolite beta catalyst having a $SiO_2/Al_2O_3$ molar ratio of 53 was prepared from the hydrogen ion form of the zeolite beta catalyst having a $SiO_2/Al_2O_3$ molar ratio of 5.

2. Preparation of 1,5-dimethyltetralin

The cyclization reaction of 5-OTP was carried out under the same reaction conditions as in Example 9, using the dealuminated zeolite beta catalyst prepared in the above 1.

The concentration of the product over the reaction time was analyzed by gas chromatography and the results thereof were shown in Table 5.

As shown in Table 5, the conversion and the selectivity were 91.3% and 89.1% at 30 minutes and 100% and 87.4% at 1 hour after initiation of the reaction, respectively, and the selectivity was 84.6% at 28 hours after initiation of the reaction.

Comparative Example 9

1,5-DMT was prepared by the cyclization reaction of 5-OTP under the same reaction conditions as in Example 9, except that the hydrogen ion form of the zeolite beta catalyst calcined at 500° C. for 4 hours and dried at 120° C. for 12 hours was used.

The concentration of the product over the reaction time was analyzed by gas chromatography and the results thereof were shown in Table 5.

As shown in Table 5, the conversion and the selectivity were 73.6% and 92.8% at 30 minutes, 82.8% and 90.9% at 1 hour, and 98.2% and 89.1% at 3 hours after initiation of the reaction, respectively, and the selectivity was 85.4% at 28 hours after initiation of the reaction.

TABLE 5

|  | Reaction time (hrs) | Example 9 | Example 10 | Comparative Example 9 |
|---|---|---|---|---|
| Conversion (%) | 0.5 | 92.2 | 91.3 | 73.6 |
|  | 1 | 100 | 100 | 82.8 |
|  | 3 | 100 | 100 | 98.2 |
|  | 28 | 100 | 100 | 100 |
| Selectivity (%) | 0.5 | 91.6 | 89.1 | 92.8 |
|  | 1 | 90.8 | 87.4 | 90.9 |
|  | 3 | 87.9 | 86.8 | 89.1 |
|  | 28 | 85.1 | 84.6 | 85.4 |
| Yield (%) | 0.5 | 84.5 | 81.3 | 68.3 |
|  | 1 | 90.8 | 87.4 | 75.3 |
|  | 3 | 87.9 | 86.8 | 87.5 |
|  | 28 | 85.1 | 84.6 | 85.4 |

TABLE 5-continued

| Reaction time (hrs) | Example 9 | Example 10 | Comparative Example 9 |
|---|---|---|---|
| Reaction temperature (° C.) | 120 | 120 | 120 |
| Total reaction time (hrs) | 28 | 28 | 28 |

Example 11

1,5-DMT was prepared in the same manner as in Example 9, except that in Example 9, the reaction temperature was 150° C.

The concentration of the product over the reaction time was analyzed by gas chromatography and the results thereof were shown in Table 6.

As shown in Table 6, the conversion and the selectivity were 100% and 88.7% at 30 minutes and 100% and 86.5% at 1 hour, and the selectivity was 82.3% at 28 hours after initiation of the reaction.

Comparative Example 10

1,5-DMT was prepared under the same reaction conditions as in Comparative Example 9, except that in Comparative 9, the reaction temperature was 150° C.

The concentration of the product over the reaction time was analyzed by gas chromatography and the results thereof were shown in Table 6.

As shown in Table 6, the conversion and the selectivity were 95.3% and 89.1% at 30 minutes and 100% and 88.2% at 1 hour, and the selectivity was 83.1% at 28 hours after initiation of the reaction.

TABLE 6

| | Reaction time (hrs) | Example 11 | Comparative Example 10 |
|---|---|---|---|
| Conversion (%) | 0.5 | 100 | 95.3 |
| | 1 | 100 | 100 |
| | 28 | 100 | 100 |
| Selectivity (%) | 0.5 | 88.7 | 89.1 |
| | 1 | 86.5 | 88.2 |
| | 28 | 82.3 | 83.1 |
| Yield (%) | 0.5 | 88.7 | 84.9 |
| | 1 | 86.5 | 88.2 |
| | 28 | 82.3 | 83.1 |
| Reaction temperature (° C.) | | 150 | 150 |
| Total reaction time (hrs) | | 28 | 28 |

According to the results shown in Tables 1 to 6, it can be confirmed that Examples 1 to 11 in which the dealuminated zeolite beta catalyst according to the present invention is used in the cyclization reaction of 5-OTP, has high conversion and high selectivity 1,5-DMT, and effects of suppressing deactivation of the catalyst, as compared to Comparative Examples 1 to 4 in which the zeolite beta catalyst having undergone no dealumination treatment is used, Comparative Examples 5 to 8 in which the platinum and copper ion-exchanged zeolite beta catalyst is used, and Comparative Examples 9 to 10 in which the hydrogen ion form of the zeolite beta catalyst is used.

The preparation method of 1,5-dimethyltetralin according to the present invention has the effects of not only showing high conversion and high selectivity of 1,5-dimethyltetralin but also of suppressing deactivation of the zeolite beta catalyst to thus enhance the catalyst life, by using the dealuminated zeolite beta catalyst.

What is claimed is:

1. A method for preparing 1,5-dimethyltetralin comprising:
    adding 5-ortho-tolylpentene to a vessel;
    adding a dealuminated zeolite beta catalyst to the vessel, wherein the dealuminated zeolite beta catalyst has a SiO2/Al2O3 molar ratio of 14 and an average particle size of 1.5 mm; and
    heating the vessel to a temperature of 120° C. at normal pressure to recover 1,5-dimethyltetralin, wherein 1,5-dimethyltetralin is recovered at a conversion % value of 100%.

* * * * *